United States Patent [19]

Kleiner

[11] Patent Number: 4,481,151

[45] Date of Patent: Nov. 6, 1984

[54] PROCESS FOR THE PREPARATION OF DIALKYLPHOSPHINIC ACID HALIDES

[75] Inventor: Hans-Jerg Kleiner, Kronberg/Taunus, Fed. Rep. of Germany

[73] Assignee: Hoechst Aktiengesellschaft, Frankfurt am Main, Fed. Rep. of Germany

[21] Appl. No.: 415,422

[22] Filed: Sep. 7, 1982

[30] Foreign Application Priority Data

Sep. 9, 1981 [DE] Fed. Rep. of Germany ....... 3135666

[51] Int. Cl.$^3$ ............................................. C07F 9/34
[52] U.S. Cl. ............................................. 260/543 P
[58] Field of Search ................................. 260/543 P

[56] References Cited

U.S. PATENT DOCUMENTS 2,994,715 6/1961 Bloch .................................. 260/543

FOREIGN PATENT DOCUMENTS 1018414 11/1957 Fed. Rep. of Germany .
2129583 12/1972 Fed. Rep. of Germany .
2225545 3/1973 Fed. Rep. of Germany .
787850 12/1957 United Kingdom .

OTHER PUBLICATIONS

Patai, Saul *The Chemistry of Acyl Halides,* (1972), Interscience, Publ. at p. 49.
Kosolapoff, Grenady M. et al., *J. Am. Chem. Soc.* vol. 73, (1951), pp. 4101–4102 and 5466–5467.

*Primary Examiner*—Natalie Trousof
*Assistant Examiner*—L. Hendriksen
*Attorney, Agent, or Firm*—Curtis, Morris & Safford

[57] ABSTRACT

Dialkylphosphinic acid halides are prepared by reaction of dialkylphosphinic anhydrides with hydrogen halide at temperatures of from about 140° to 250° C. The hydrogen halide—preferably hydrogen chloride or bromide—is advantageously introduced in excess at a rate of from about 3 to 10 mols per mol of dialkylphosphinic anhydride an hour into the anhydride which is liquid or dissolved in an inert solvent.

The reaction products are mainly intermediates in the field of plant protection and flameproofing agents.

8 Claims, No Drawings

PROCESS FOR THE PREPARATION OF DIALKYLPHOSPHINIC ACID HALIDES

Dialkylphosphinic acid halides are compounds of the formula

in which $R_1$ and $R_2$ each are alkyl, and X is halogen.

They are mainly intermediates, especially in the field of plant protection and fireproofing agents.

A series of different methods is known for their preparation. One of them is for example described in Houben-Weyl, Methoden der organischen Chemie, Stuttgart 1963, vol. XII/1, p. 241; according thereto dialkylphosphinic acids are converted to the corresponding dialkylphosphinic acid chlorides with phosphorus pentachloride $PCl_5$ or thionyl chloride $SOCl_2$:

$$\underset{R_2}{\overset{R_1}{\diagdown}}\!\!\overset{O}{\underset{\|}{P}}\!-OH + PCl_5[SOCl_2] \longrightarrow$$

$$\underset{R_2}{\overset{R_1}{\diagdown}}\!\!\overset{O}{\underset{\|}{P}}\!-Cl + POCl_3[SO_2] + HCl$$

According to this reference, instead of the free dialkylphosphinic acids the alkyl esters thereof may alternatively be used. In this case, however, only $PCl_5$ is indicated as halogenating agent:

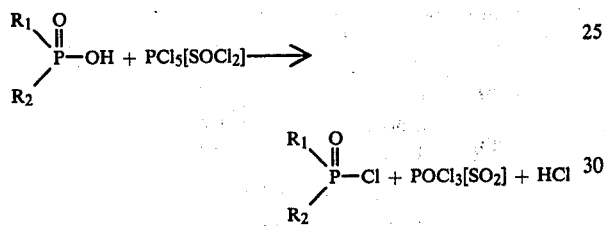

In this reaction, the corresponding dialkylphosphinic anhydrides are said to occur sometimes as by-products, which is probably due to further reaction of the dialkylphosphinic acid chlorides formed in the main reaction with unreacted starting material:

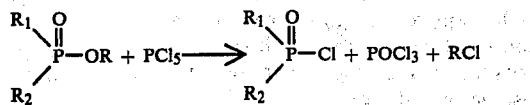

According to p. 226 of this reference, a process for the preparation of dialkylphosphinic anhydrides is based on this reaction (reaction temperature about 150° to 160° C.).

This reference discloses furthermore the preparation of diphenylphosphinic anhydride by heating diphenylphosphinic acid to 230° C.:

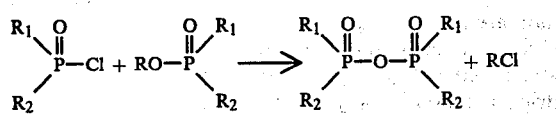

Processes rather similar to the above methods for the preparation of dialkylphosphinic acid halides are described in German Offenlegungsschrift No. 2,129,583 and its addition No. 2,225,545, according to which dialkylphosphinic acid alkyl esters (German Offenlegungsschrift No. 2,129,583) and the free dialkylphosphinic acids or the alkali metal or ammonium salts thereof (German Offenlegungsschrift No. 2,225,545) are reacted with halides of carbonic acid (especially phosgene) or oxalic acid, or with thionyl halides; the reaction temperatures indicated ranging from −20° to 150° C. The reaction is said to proceed via the corresponding dialkylphosphinic anhydrides, which can be isolated, too. The following scheme (similar to the above reactions) illustrates the course of the reaction; phosgene being used as example of halogenating agent:

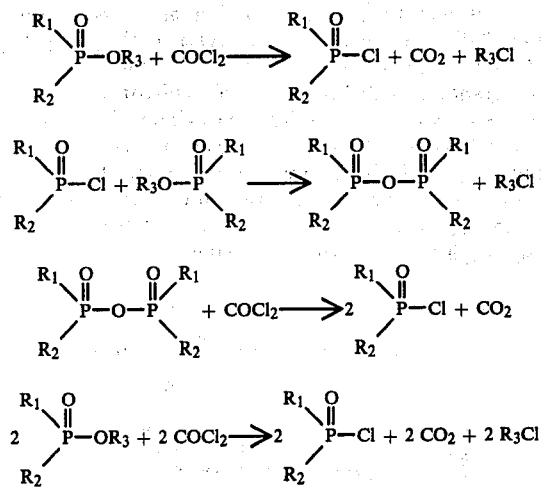

[$R_1$, $R_2$=Alkyl (G.O.S. 2,129,583), $R_3$=H, alkali metal or $NH_4$ ion (G.O.S. 2,225,545)]

Although the known processes for the manufacture of dialkylphosphinic acid halides give high yields and have other advantages, too, they need improvement especially in view of their application in an industrial scale; for, the inorganic acid halides are a considerable element of cost. Furthermore, handling or these acid halides is not easy (especially in the case of the very toxic $COCl_2$ phosgene), either, and some of them yield products (phosphorus oxyhalides!) which cannot be separated from the dialkylphosphinic acid halides formed in the reaction but with difficulty.

It was therefore the object of the invention to improve the known processes or to find a novel, more economic process for the preparation of dialkylphosphinic acid halides. This object is achieved by reaction of dialkylphosphinic anhydrides with hydrogen halide at elevated temperature.

Subject of the invention is therefore a process for the preparation of dialkylphosphinic acid halides by reaction of dialkylphosphinic anhydrides with an inorganic halogen compound at elevated temperature, which comprises using hydrogen halide as inorganic halogen compound, and carrying out the reaction at a temperature of from about 140° to 250° C., preferably about 170° to 220° C.

The reaction proceeds according to the following scheme:

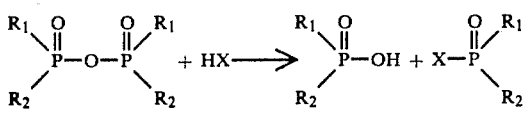

($R_1$, $R_2$ = alkyl, X = halogen)

With the use of the simplest halogen compounds, practically quantitative yields, relative to reacted starting material, are so obtained. This was extremely surprising, because due to the known dehydration of diphenylphosphinic acid to its anhydride at 230° C. (see Houben-Weyl, Methoden der organischen Chemie, vol, XII/1, 1963, p. 266) it was to be expected that there is practically no result when reacting phosphinic anhydrides in a similar temperature range in the presence of hydrogen halide. For, on the basis of the above reaction scheme, it was to be expected that at temperatures around 200° C., especially in the presence of hydrogen halide which is known for its very dehydrating effect, the corresponding dialkylphosphinic anhydride would be formed anew from the free dialkylphosphinic acid obtained first, and the water formed in this reaction would react with the dialkylphosphinic acid halide to give the corresponding anhydride, too. The course of the reaction as expected according to the state of the art is illustrated by the following scheme:

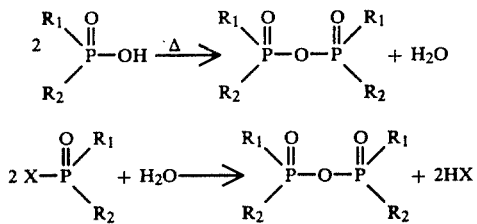

However, the reaction according to the invention proceeds not at all in this manner.

Suitable starting substances for the process of the invention are in principle any dialkylphosphinic anhydrides, preferably, however, those having alkyl radicals with up to 6 carbon atoms at most, especially up to 4 carbon atoms only, such as for example dimethyl-, diethyl-, ethylmethyl-, methylpropyl-, methylpentyl-, dipropylphosphinic anhydride.

The anhydrides are prepared in known manner, for example as described in German Offenlegungsschrift No. 2,129,583 and 2,225,545 (from dialkylphosphinic acid esters, the free dialkylphosphinic acids or the salts thereof, and the halides of carbonic or oxalic acid, or thionyl halides) or German Offenlegungsschrift No. 2,758,580 (from free dialkylphosphinic acids and aliphatic carboxylic anhydrides, especially acetic anhydride). As hydrogen halide, hydrogen chloride HCl or bromide HBr are preferably used. In this case, the corresponding dialkylphosphinic acid chloride or bromide is obtained according to the process of the invention.

It is recommended to introduce the hydrogen halide in excess at a rate of about 3 to 10, preferably about 4 to 6, mols per mol of dialkylphosphinic anhydride, which may alternatively be dissolved in an inert solvent. These inert, correspondingly high-boiling solvents are used especially in those cases where the starting anhydrides have an elevated molecular weight (in the case of long alkyl radicals $R_1$ and $R_2$) per hour into the liquid dialkylphosphinic anhydride.

The reaction can be carried out under various pressure, for example a pressure of about 5 to 10 bar; normal pressure being however preferred. The dialkylphosphinic acid halide formed in the reaction is distilled off at the reaction temperature chosen in the excess hydrogen halide current together with small amounts of starting substance (anhydride) and possibly the corresponding phosphinic acid. It is therefore recommended to subject the crude distillates to a purification distillation, advantageously immediately after their obtainment and to the extent to which they are formed. Residue of the crude distillates is mainly phosphinic anhydride which is recycled to the process. The residue of the reaction consists of phosphinic adids which are converted in known manner (preferably according to the process of German Offenlegungsschrift No. 2,758,580) to the anhydrides.

The process of the invention can be carried out either continuously or batchwise.

Because of the use of practically the simplest halogenating agent (hydrogen halide) and the practically quantitative reaction, the process of the invention brings about a considerable progress in this field. In the case where the dialkylphosphinic anhydrides used as starting substances are prepared without the use of inorganic acid halides (that is, according to the process of German Offenlegungsschrift No. 2,758,580), no inorganic acid halides at all are needed for obtaining the intended dialkylphosphinic acid halides.

The following examples illustrate the invention.

EXAMPLE 1

200 g of ethylmethylphosphinic anhydride (1.01 mols) are heated with stirring to 200° C. Subsequently, hydrogen chloride is introduced in excess (rate of introduction about 200 g/hour=5.5 mols/mol of ethylmethylphosphinic anhydride per hour). In a receiver, a distillate is collected which is distilled portionwise in a water jet vacuum. The distillation residues are ethylmethylphosphinic anhydride and are recycled to the reaction batch. After about 8 hours, 80 g of ethylmethylphosphinic acid chloride are obtained. 155 g remain as residue, which consists of 67.5 g of ethylmethylphosphinic acid, 75 g of ethylmethylphosphinic anhydride and 12.5 g of hydrogen chloride. This corresponds to a conversion rate of 63% and a yield of about 100% of theory, relative to reacted starting material.

EXAMPLE 2

200 g of methylpropylphosphinic anhydride (0.886 mol) are heated with stirring to 195°–200° C. Hydrogen chloride is then introduced in excess (introduction rate about 200 g/hour=6 mols/mol of phosphinic anhydride per hour). In a receiver a distillate is collected which is distilled portionwise in a water jet vacuum. The distillation residues are methylpropylphosphinic anhydride and are recycled to the reaction batch. After about 10 hours, 72 g of methylpropylphosphinic acid chloride (b.p. 122° C./3.47 kPa) are obtained, which corresponds to a conversion rate of about 58% of theory. Taking into consideration the amount of methylpropylphosphinic anhydride and acid remained in the residue, the yield is about 100% of theory, relative to reacted starting material.

EXAMPLE 3

100 g of methylpropylphosphinic anhydride (0.443 mol) are heated to 200° C. with stirring. Hydrogen bromide is then introduced (rate about 170 g/hour=about 4.8 mols/mol of phosphinic anhydride per hour). In a receiver a distillate is collected which subsequently is distilled in vacuo. After 6 hours, 35 g of methylpropylphosphinic acid bromide (b.p. 75° C./0.107 kPa) are obtained, which corresponds to a conversion rate of about 43% of theory. Taking into consideration the amount of methylpropylphosphinic anhydride and -acid remaining in the residue, the yield is about 100% of theory, relative to reacted starting material.

What is claimed is:

1. A process for the preparation of a dialkyl phosphinic acid halide of the formula

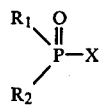

in which $R_1$ and $R_2$, independently from each other, are alkyl radicals having from 1 to 6 carbon atoms and X is a halogen atom, which comprises:

introducing hydrogen halide at a reaction temperature of from about 170° to 220° C. and at normal pressure into a dialkyl phosphinic anhydride of the formula

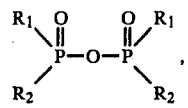

in which $R_1$ and $R_2$ have the same meaning as in the formula for the dialkyl phosphinic acid halide; and
distilling off at the reaction temperature the dialkyl phosphinic acid halide formed in the reaction.

2. A process as recited in claim 1, wherein the hydrogen halide is hydrogen chloride or hydrogen bromide.

3. A process as recited in claim 2, wherein the hydrogen halide is introduced in excess at a rate of from about 3 to 10 mols per mol of dialkyl phosphinic anhydride per hour.

4. A process as recited in claim 2, wherein the hydrogen halide is introduced in excess at a rate of from about 4 to 6 mols per mol of dialkyl phosphinic anhydride per hour.

5. A process as recited in claim 1, wherein $R_1$ and $R_2$ are alkyl radicals having from 1 to 4 carbon atoms.

6. A process as recited in claim 5, wherein the hydrogen halide is hydrogen chloride or hydrogen bromide.

7. A process as recited in claim 6, wherein the hydrogen halide is introduced in excess at a rate of from about 3 to 10 mols per mol of dialkyl phosphinic anhydride per hour.

8. A process as recited in claim 6, wherein the hydrogen halide is introduced in excess at a rate of from about 4 to 6 mols per mol of dialkyl phosphinic anhydride per hour.

* * * * *